United States Patent [19]

Dugas

[11] 4,299,251
[45] Nov. 10, 1981

[54] OPTICAL VALVE POSITION SENSING

[75] Inventor: Roger A. Dugas, Chester, N.H.

[73] Assignee: Hewlett-Packard Company, Palo Alto, Calif.

[21] Appl. No.: 72,515

[22] Filed: Sep. 4, 1979

[51] Int. Cl.³ .................... F16K 37/00; F16K 11/085
[52] U.S. Cl. ............................... 137/556; 137/625.47; 137/554; 137/555; 128/675; 250/227
[58] Field of Search ......................... 250/231 SE, 227; 137/554, 555, 556, 625.41, 625.47; 128/673–675

[56] References Cited

U.S. PATENT DOCUMENTS

| | | | |
|---|---|---|---|
| 2,955,283 | 10/1960 | Busch-Keiser | 250/231 SE |
| 3,276,472 | 10/1966 | Jinkens et al. | 137/556 |
| 3,610,228 | 10/1971 | Temkin | 128/673 |
| 3,633,616 | 1/1972 | Meshek | 137/554 |
| 3,731,107 | 5/1973 | Goodwin et al. | 250/227 |
| 3,761,719 | 9/1973 | Stoever | 250/227 |
| 4,088,387 | 5/1978 | Lewis | 250/227 |
| 4,112,272 | 9/1978 | Jonsson et al. | 128/675 |
| 4,156,437 | 5/1979 | Chivens et al. | 137/554 |

*Primary Examiner*—Martin P. Schwadron
*Assistant Examiner*—A. Michael Chambers
*Attorney, Agent, or Firm*—Donald N. Timbie

[57] ABSTRACT

Apparatus for indicating the position of a rotary valve contained in a disposable lid including light reflecting means mounted to rotate as the valve rotates, light sources mounted on a permanent base for directing light toward the light reflecting means, light transducing means mounted in the permanent base so as to receive light reflected by said reflecting means, and circuits coupled to said sources and transducing means for producing signals indicating the rotary position of the valve.

6 Claims, 6 Drawing Figures

U.S. Patent
Nov. 10, 1981
4,299,251
FIG 1
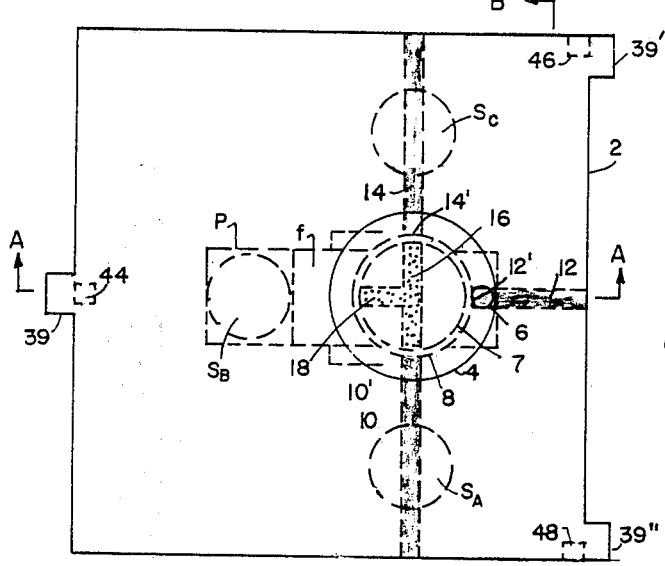
FIG 1B
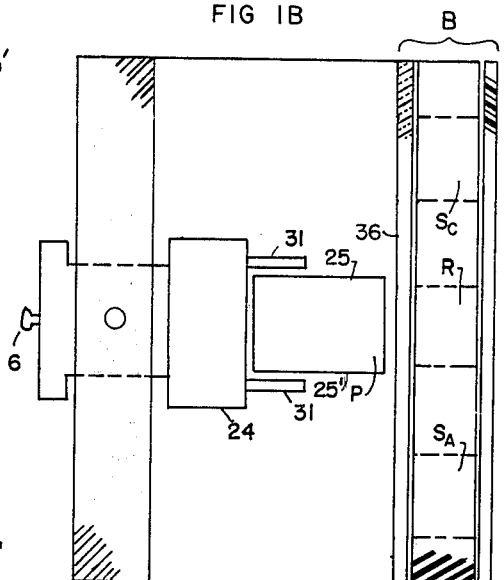
FIG 1A
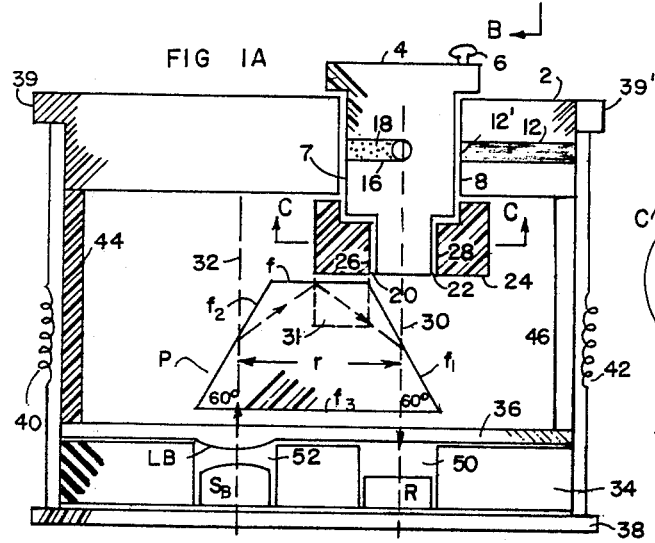
FIG 2
FIG 1A'
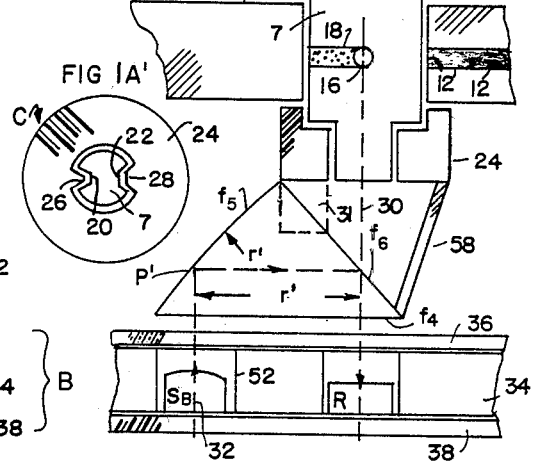
FIG 3
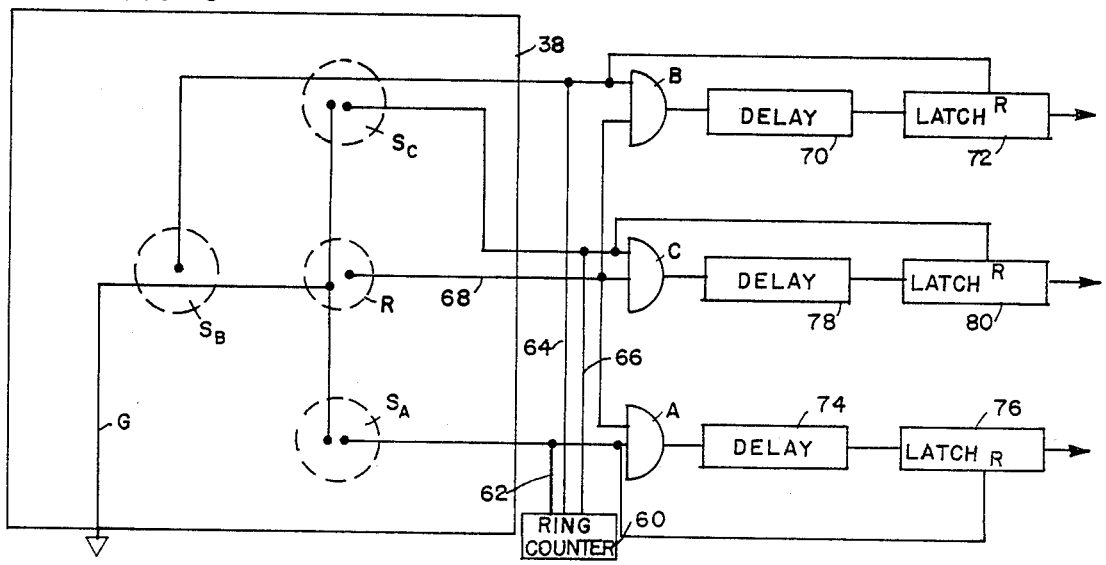

OPTICAL VALVE POSITION SENSING

BACKGROUND OF THE INVENTION

In monitoring blood pressure, it is customary to insert one catheter to monitor arterial pressure and another catheter to monitor venous pressure. Each catheter is connected to a separate manually-operated rotary valve that can be positioned so as to couple the column of fluid in its catheter to a transducer or to means for withdrawing a sample of blood. Knowledge of the positions of the valves is necessary not only for the purpose of making a proper analysis of the varying blood pressures indicated by the transducer but also for the proper setting of low blood pressure alarms. For example, if the transducer is coupled to the venous catheter, the alarm should be set to sound at a much lower pressure than if the transducer is coupled to the arterial catheter. Neither alarm should sound if the valve is turned to shut off the blood pressure from the transducer so as to permit the withdrawal of a sample.

Whereas the positions of the valves can be determined by visual inspection, this can be confusing, especially if there is a change in operators. Furthermore, a manually operated system does not permit the use of monitoring instrumentation that is programmed to automatically set up alarm levels and to provide messages as to errors in valve settings when certain procedures are keyed into it.

BRIEF DISCUSSION OF THE INVENTION

This invention overcomes the problems enumerated above by provision of a system that produces a unique electrical signal for each position of a valve. The signal can be used to indicate valve positions to the operator in a more noticeable manner than the physical position of the valve itself or they can be used to inform the monitoring instrument.

Instead of sterilizing the valves and associated components after each use, they are generally disposed of for economic reasons. Therefore, any portion of a valve positioning system that is to be disposed of along with the valves must be inexpensive. This is achieved by this invention in the following manner. A light reflecting means is mounted so as to rotate as the valve rotates. In a first form, sources of light are located at positions in the permanent base of the instrument such that light from only one source is reflected to a light transducer or transducers mounted in the base when the valve is in a given rotational position. Means are provided for enabling the light sources in repeated sequence and inasmuch as light from only one source can be reflected by the light reflecting means to a transducer, the valve position can be determined by the coincidence of the enabling of a light source and the appearance of an electrical signal from the transducer or transducers. In a second form of the invention, the positions of the light sources and the transducers are reversed so that the transducers are enabled in repeated sequence. Identification of the position of the valve is determined by the presence of an electrical signal at the output of a transducer. Because light transducers are more expensive than light sources at the present time, the first embodiment described is preferred.

A number of variations of either form are possible, e.g., the light reflecting means can be coupled so as to rotate with the valve or it can preferably be mounted directly to the valve. In either case, the axis of rotation of the light reflecting means can coincide with the direction along which light is received or reflected or it can be between these directions or outside of them. It is generally preferable, however, that the path followed by light from a source toward the reflecting means and the path of the reflected light be parallel and that one of them coincides with the axis of rotation of the light reflecting means.

THE DRAWINGS

FIG. 1 is a top view of a valve assembly utilizing the invention;

FIG. 1A is a section AA of FIG. 1;

FIG. 1A' is a partial section CC of FIG. 1A;

FIG. 1B is a side elevation of FIG. 1 taken at BB;

FIG. 2 is a section like AA of FIG. 1A illustrating the use of a differently shaped prism as part of the optical system; and FIG. 3 is a schematic diagram of circuits for use with the valve assembly of FIG. 1.

DESCRIPTION OF A PREFERRED EMBODIMENT

FIG. 1 is a top view of a disposable lid 2 showing the top plate 4 and knob 6 of a rotary valve that, as best seen in FIG. 1A, has a stem 7 of smaller diameter than the top plate 4 that extends with a friction fit through a cylindrical hole 8 in the lid 2. Because the clearance between the stem 7 and the hole 8 has been exaggerated for purposes of illustration, they are indicated by separate dashed circles 7 and 8 in FIG. 1. Passageways 10, 12 and 14, that are shaded for purposes of illustration, are formed within the lid 2 and respectively extend from openings 10', 12' and 14' in the wall of the hole 8 to the outer edges of the lid 2. The openings 10', 12' and 14' are in a plane perpendicular to the axis of the hole 8 and 90° apart. Within the stem 7, there is a diametric channel 16 that intersects a radial channel 18, both of which are dotted in the drawings. When the valve is in the rotational position shown in FIG. 1, the diametric channel 16 within the stem 7 provides communication between the openings 10' and 14' that are respectively at the ends of the passageways 10 and 14 in the lid 2. The knob 6 is always nearest the passageway that is not connected to anything, which in FIG. 1 is the passageway 12. Clockwise rotation by 90° connects the passageways 12 and 14 in the lid 2 via the radial channel 18 and half of the diametric channel 16, and counterclockwise rotation by 90° connects the passageways 10 and 12 in the lid 2 via the other half of the diametric channel 16 and the radial channel 18.

As best seen in FIG. 1A and FIG. 1A', the lower end of the stem 7 projects below the lid 2 and has diametrically opposed keyways 20 and 22 that are parallel to its axis. A washer 24 is provided with a central opening of such diameter that it can be press fit over the lower end of the stem 7. The washer 24 has diametrically opposed axial keys 26 and 28 that respectively fit into the keyways 20 and 22 when the washer 24 is oriented so as to permit the top of the washer 24 to come close to the underside of the lid 2. Because the keyways 20 and 22 and the keys 26 and 28 that fit in them are of respectively different sizes, as shown in FIG. 1A', the washer 24 can be properly mounted in only one angular position.

A light reflecting means in the form of a trapezoidal prism P that is solid and transparent is attached to the underside of the washer 24 in such manner that one sloping face $f_1$ of the prism P intersects the axis 30 of the valve stem 7 and the top plate 4. Although various methods for attaching the prism P to the washer 24 may be used, it is important that no supporting structure touches the outer faces f, $f_1$ or $f_2$ of the prism P because this would interfere with the internal reflection to be described. Face $f_3$ must be left untouched by structure to allow the light beam to pass into and out of the prism P. Therefore, as shown in FIG. 1B, the sides 25 and 25' of the prism P are respectively held by two tabs 31 and 31' that extend below the washer 24.

As the stem 7 is rotated, the center of the face $f_1$ continues to intersect the axis 30 and the center of the opposite sloping face $f_2$ of the prism P that intersects a line 32 that is parallel to the axis 30 will follow a circular locus having the radius r indicated in FIG. 1A. The respective angles of the sloping faces $f_1$ and $f_2$ with respect to the axis 30 and the line 32 and the angle of the upper face f with respect to the axis 30 and the line 32 are such that light directed upwardly through the underface $f_3$ of the prism P along the axis 30 or the line 32 will be totally and internally reflected so as to emerge downwardly along the other.

A permanent base B to which the disposable lid 2 is removably attached may be mounted in a housing, not shown, and is comprised of a plate 34 made from insulating material, a transparent sheet 36 resting on the upper side of the plate 34, and a printed circuit board 38 at its bottom. The lid 2 is removably attached to the base B by springs 40 and 42 respectively connected between projections 39 and 39' on the lid 2 and the board 38, as shown in FIG. 1A, and a spring, not shown, that is connected between the projection 39" and the board 38. The lid 2 is spaced from the base B by three posts 44, 46 and 48 located as shown in FIG. 1. The posts 44, 46 and 48 may be attached to the lid 2 or to the transparent sheet 36. The spacing is such that the upper surface of the sheet 36 is parallel to and a small distance away from the lower face $f_3$ of the prism P. A light transducer R that translates light impinging on its upper surface into electrical signals is centered on the axis 30 in a hole 50 in the plate 34. Light sources $S_A$, $S_B$ and $S_C$, which may be LEDs, are mounted in holes in the plate 34 with their centers at a distance r from the axis 30 at each of the switch positions as indicated by the dashed circles $S_A$, $S_B$ and $S_C$ of FIG. 1. In FIG. 1A, only one light source, $S_B$, is seen. It is mounted in a hole 52 in the plate 34. As indicated by the prism which is depicted by the dashed rectangle P in FIG. 1, the valve is shown in a position where the diametrical channel 16 in the stem 7 interconnects the passageways 10 and 14 in the lid 2. In this position, the line 32 is centered on the source $S_B$, and light from the source $S_B$ is internally reflected by the faces $f_2$, f and $f_1$ of the prism P, as shown by the dashed line, to the transducer R.

Although they may not be absolutely necessary, collimating lenses in the form of spherically shaped protrusions from the bottom of the transparent sheet 36 are located in registration with the holes containing the light sources $S_A$, $S_B$ and $S_C$. In FIG. 1A, only the lens $L_B$ for the source $S_B$ can be seen.

In order that light from each of the sources $S_A$, $S_B$ and $S_C$ may be directed down the axis 30 to the transducer R when the center of the face $f_2$ is in registration with their respective centers, light must approach each of the faces $f_2$, f and $f_1$ at angles greater than the critical angle, and this must occur even when liquids such as a 0.9% solution of saline or a 5% solution of dextrose that are generally present come in contact with the outer surfaces of the prism P. The angles indicated in FIG. 1A have been found satisfactory for a trapezoidal prism.

Another variation of the prism is the special triangular prism P', illustrated in FIG. 2, in which parts corresponding to those of other figures of the drawings are designated by the same numerals or letters. Note, however, that the spherical lenses formed in the bottom of the sheet 36 of FIG. 1A are omitted and that the face $f_4$ of the prism P' is spherical with a radius r' so as to perform the collimating or focussing function. Light from the source $S_B$ follows the dashed line through the face $f_4$ to the spherical face $f_5$ that reflects it to a face $f_6$ which reflects it downwardly along the axis 30. A strut 58 is connected between the lower right corner of the prism P' and the washer 24 so as to provide strength.

The schematic diagram of FIG. 3 illustrates a system for indicating the valve position by identifying which of the light sources $S_A$, $S_B$ and $S_C$ are in registration with the center of the face $f_2$ of the prism P. On the printed circuit board 38, ground connections are made available to the light sources $S_A$, $S_B$ and $S_C$ and to the light transducer R by a ground conductor G. A ring counter 60 supplies voltage pulses in repeated sequence to points on the circuit board 38 where they can be made available to the light sources $S_A$, $S_B$ and $S_C$ via conductors 62, 64 and 66 respectively. These pulses are also respectively applied to inputs of AND gates A, B and C. A conductor 68 that is connected to receive electrical signals provided by the receiver R when light impinges on it is connected to the other inputs of the AND gates. Thus, when the valve is positioned so that the center of the face $f_2$ of the prism P is over the source $S_B$, as shown in FIG. 1A, the passageways 10 and 14 in the lid 2 are interconnected, and both inputs of the AND gate B receive a signal causing it to output a high state voltage via a delay means 70 to a latch 72. Connection of the conductor 64 from the counter 60 to the reset input of the latch 72 causes it to be reset each time the source $S_B$ is energized. The purpose of the delay 70 is to insure that resetting takes place before the output of the AND gate B sets the latch 72. Between pulses on the lead 64, the output of this latch indicates that the valve is in a position such that the face $f_2$ of the prism P is over the source $S_B$. The other AND gates A and C do not output a high state voltage because the receiver R does not output a signal on lead 68 when the sources $S_A$ and $S_C$ are respectively energized. This is because no light is directed from these sources to the receiver R by the prism P.

The output of the AND gate A is coupled via a delay 74 to a latch 76 having its reset input R connected to the lead 62, and the output of the AND gate C is coupled via a delay 78 to a latch 80 having its reset input R connected to the lead 66. When the face $f_2$ os the prism P is over the source $S_A$, the valve interconnects passageways 10 and 12 in the lid 2, and the output of the AND gate A, as well as the output of the latch 76, is high. When the face $f_2$ of the prism P is over the source $S_C$, the valve interconnects passageways 12 and 14 in the lid 2 and the output of the AND gate C, as well as the output of the latch 80, is high.

ALTERNATIVE EMBODIMENT

If, for any reason, it should be desirable to use one light source and a plurality of light transducers, a light transducer would be substituted for each of the light sources $S_A$, $S_B$ and $S_C$ and a light source directing light upward along the axis 30 would be substituted for the light transducer R. The ring counter 60, its leads 62, 64 and 66, the delays 70, 74 and 78, as well as the latches 72, 76 and 80, can be eliminated. All that is required in addition is means for applying a high state voltage on the lead 68 and a light source in the place of the receiver R that can be lit by such voltage. With such an arrangement, one input of all the AND gates A, B and C is always at a high state and the only AND gate having its other input at a high state is the one corresponding to the position of the prism P and therefore of the valve. In FIG. 1A, the output of the AND gate B would be high, and the outputs of the other AND gates A and C would be low.

What is claimed is:

1. A disposable valve structure, comprising
a lid,
means defining a cylindrical hole in said lid, said hole having an axis,
means defining passageways in said lid respectively communicating with the cylindrical wall of said hole at respective various points that are angularly displaced around its cylindrical periphery,
a valve body having a cylindrical stem mounted for rotation about its axis in said hole, its axis coinciding with the axis of said hole, said stem containing channel means for communicating between said passageways at said various points, said channel means including respective openings angularly displaced around its cylindrical outer surface so as to provide communication between selected ones of said passageways in said lid depending on the rotational position of said valve body, and
a light reflecting means including means mounting said light reflecting means so as to allow said light reflecting means to rotate about a given axis corresponding to the rotation of said valve body about its axis, said light reflecting means reflecting light which may approach it along one path into a direction away from it along another path that is spaced from and parallel to said one path, one of said paths being coextensive with the given axis about which said light reflecting means rotates, said valve structure being adaptable such that light passing toward the light reflecting means along one path and out the other may be used to determine the rotational position of said valve body.

2. A disposable valve structure as set forth in claim 1 wherein the axis of rotation of said light reflecting means coincides with the axis of rotation of said valve stem.

3. In combination with the disposable valve structure set forth in claims 1 or 2,
a base removably attached to said lid and mounted on the opposite side of said light reflecting means from said lid,
a light transducer affixed to said base so as to be responsive to light in the path that coincides with said given axis of rotation of said light reflecting means, means mounted at each of a plurality of points for projecting light parallel to the axis of rotation of said light reflecting means and toward said reflecting means along the other of said paths successively and in repeated sequence along the circular locus traced by the other of said paths as a result of rotation of said light reflecting means, each of said plurality of points respectively corresponding to the rotational position of said valve body when the channel means contained therein provides communication between selected passageways in said lid, and
means for determining the rotational position of said valve body by the coincidence of said projected light from one of said light projecting means and an electrical signal produced by said transducer when said projected light is received by said transducer.

4. In combination with the disposable valve structure set forth in claims 1 or 2,
a base removably attached to said lid and mounted on the opposite side of said light reflecting means from said lid,
means for projecting light successively in a repeated sequence toward said light reflecting means along the one of said paths that coincides with said given axis of rotation of said light reflecting means,
electrical light transducers respectively mounted at each of a plurality of points along the circular locus traced by the other of said paths as a result of the rotation of said light reflecting means, each of said plurality of points respectively corresponding to the rotational position of said valve body when the channel means contained therein provides communication between selected passageways in said lid, and
means for determining the rotational position of said valve body by the coincidence of said projected light from said light projecting means and an electrical signal from one of said transducers when said light is received by said one of said transducers.

5. A disposable valve structure as set forth in claims 1 or 2 in which said light reflecting means is a prism made of solid transparent material having at least three faces, a first face mounted so as to be intersected by one of said paths, a second face mounted so as to be intersected by the other of said paths, the internal angles between the faces being such that when light along either of said paths strikes a respective face at an angle less than the critical angle, said light is reflected along the other of said paths.

6. A multiposition valve assembly that produces a signal indicative of the position of the valve, comprising
a lid,
means defining a cylindrical hole in said lid, said hole having an axis,
means defining passageways in said lid respectively communicating with the cylindrical wall of said hole at respective points angularly displaced around its periphery,
a valve body having a cylindrical valve stem mounted for rotation about its axis in said hole, its axis coinciding with the axis of said hole, said stem containing channel means communicating with said respective points that are angularly displaced around its cylindrical outer surface so as to provide communication between selected passageways in said lid via said channel means depending on the rotational position of the valve body,
light reflecting means for reflecting light approaching it along a first path into a direction away from it along a second path that is spaced from and parallel to said first path,
means mounting said light reflecting means to said valve stem so that said second path is coextensive with the axis of said valve stem,
a base, means for removably attaching said base to said lid so that said light reflecting means is between them, light sources affixed to said base at points on the locus of the intersection of said first path of said light reflecting means as it revolves about its second path, said light sources emanating a beam of light in a direction parallel to said first path, the angular spacing about said first path of said light sources corresponding to the angular spacing about the axis of said stem of the points at which the passageways in said lid communicate with the cylindrical wall of said hole, a light receiver that produces an electrical signal when light impinges on it mounted on said base so as to receive light leaving said light reflecting means along said second path, means for applying electrical energizing pulses to said sources so as to cause them to respectively emanate light in a repeated sequence, and means for producing a separate electrical output signal in response to the coincidence of each of said energizing pulses and an electrical signal produced by said receiver.

* * * * *